(12) United States Patent
Singh et al.

(10) Patent No.: US 6,258,816 B1
(45) Date of Patent: *Jul. 10, 2001

(54) ANTI-ALLERGY ANTI-INFLAMMATORY COMPOSITION

(75) Inventors: Amarjit Singh; Rajesh Jain, both of New Delhi (IN)

(73) Assignee: Panacea Biotec Limited, New Delhi (IN)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/178,652

(22) Filed: Oct. 26, 1998

(30) Foreign Application Priority Data

Nov. 6, 1997 (IN) .............................................. 3185/DEL/97

(51) Int. Cl.⁷ ........................ A61K 31/495; A61K 31/34; C07D 307/78; C07D 307/87
(52) U.S. Cl. ......................... 514/255; 514/469; 514/310; 549/462
(58) Field of Search .................................... 514/255, 469, 514/310; 549/462

(56) References Cited

U.S. PATENT DOCUMENTS

| | | | |
|---|---|---|---|
| 4,617,407 | * 10/1986 | Young et al. | 549/462 |
| 4,783,465 | * 11/1988 | Sunshine et al. | 514/255 |
| 5,587,374 | * 12/1996 | Perboni et al. | 514/210 |
| 5,627,183 | * 5/1997 | Gray | 514/255 |
| 5,688,829 | * 11/1997 | Jain et al. | 514/605 |
| 5,716,609 | * 2/1998 | Jain et al. | 424/78.05 |
| 6,017,932 | * 1/2000 | Singh et al. | 514/321 |

* cited by examiner

*Primary Examiner*—Gary Geist
*Assistant Examiner*—Everett White
(74) *Attorney, Agent, or Firm*—Oblon, Spivak, McClelland, Maier & Neustadt, P.C.

(57) ABSTRACT

A novel composition of Nimesulide and salts thereof and Cetrizine possessing antileukotriene, antihistaminic, antiallergic and antiinflammatory action is disclosed. The composition is useful in the cure of allergic disorders such as rhinitis, bronchitis, asthama, urticaria and the like.

11 Claims, No Drawings

ANTI-ALLERGY ANTI-INFLAMMATORY COMPOSITION

TECHNICAL FIELD

The present invention relates to a novel antileukotriene, antihistaminic, antiallergic and antiinflammatory composition of non-steroidal antiinflammatory sulfonanilide and, salts thereof with second generation anti-histamines ($H_1$, blockers).

More particularly the invention relates to a novel composition of Nimesulide and Cetirizine in a pharmaceutically acceptable combination in a suitable pharmaceutical base acceptable and excipients.

More particularly the invention relates to a composition for use in allergic disorders namely rhinitis, bronchitis, asthma, urticaria and the like.

BACKGROUND OF THE INVENTION

The clinical symptoms produced in the course of allergic reaction are the result of an early specific immune response and a late inflammatory reaction. The inhaled allergens (e.g. pollens, mite dust) mediate the early phase by stimulating high affinity immunoglobulin ($I_gE$) receptors e.g. mast cells and basophils which in turn release histamine and cytokines. This early phase lasts for about 30 minutes. The cytokines released from mast cells and basophils then mediate the late phase by recruiting inflammatory cells into the nasal and upper respiratory tract passages (Serafin, WE, In Goodman and Gillmans "The Pharmacological Basis of Therapeutics", Hardmen, Ja; Limbird, L,E eds, Mc Graw-Hill, N.Y., 1996, 659–682). The influx of eosinophils, macrophages, lymphocytes, neutrophils and platelets starts the vicious inflammatory cycle. This late phase lasting for 8–48 hours amplifies the initial immune response which in turn triggers the release of more inflammatory cells (Townley RG and Okada, C, *Annals of Allergy,* 68, 1991, 190–196).

Seasonal allergic rhinitis (hay fever) is caused by deposition of allergens on the nasal mucosa resulting in an immediate hypersensitivity reaction. If the allergens (e.g. dust mite) are carried to the lower airways (i.e. bronchioles), in susceptible subjects, the result is bronchoconstriction of the airways (i.e. asthma). The allergen-induced release of leukotrienes, the 5-lipoxygenase products of arachidonic acid metabolism in activated airway cells, is critical in the pathophysiology of asthma. Leukotrienes are produced by mast cells, eosinophils, neutrophils and alveolar macrophages. The use of specific leukotriene receptor antagonists or 5-lipoxygenase pathway inhibitors results in increased airflow and reduction of symptoms in asthmatic patients (Henderson W R, Jr., *Annals of Allergy,* 72, 1994, 272–277). Immunologic concepts of asthma and related allergic disorders are undergoing revolutionary changes. All asthma are now proposed to have an allergic basis and all chronic allergic disorders have a basal ongoing inflammation which is never fully resolved. In the annual meeting of the European Academy of Allergy and Clinical Immunology which took place in Greece, Jun. 1–5, 1997, the clinical implications of minimal persistent inflammation (MPI) have been emphasized. A mild presence of inflammatory cells and ICAM—1 receptors on epithelial cells has been demonstrated even during asymptomatic periods in allergic subjects. So the correct treatment of allergic disorders should address allergic inflammation and not just the symptoms. In this annual meeting a redefinition of allergic disorders was also emphasized. Rhinitis and asthma were pooled together as the inflammatory mechanisms represent a common unifying concept for the pathogenesis of allergic disorders. Allergic rhinitis and bronchial asthma frequently co-exist. Upto 40% of rhinitics have concomitant asthma and up to 80% of asthmatics also have rhinitis. Rhinitics have upto three fold greater risk of developing asthma as the inflammatory mediators, constantly being released in the airways, may produce alterations in the airway epithelium such that an allergic person becomes prone to asthmatic attacks (Wenzel, S. E, *Annals of Allergy,* 72, 1994, 261–271). It was thus proposed that treating nasal and airway inflammation may be a key to asthma control. It was concluded that development of therapeutic strategies for the prevention and prophylaxis of respiratory allergy should be approached rather than the treatment except for asthmatic emergencies.

Thus it is self-evident that although antihistamines (second generation $H_1$-blockers) are the most widely used agents for the treatment of allergic conditions (Gong, H, Tashkin, D. P, Dauphinee, B et al., *J.Allergy. Clin. Immunol.,* 85, 1990, 632–641), NSAIDS can also prove to be very useful as anti-inflammatory drugs. To date, NSAIDS like aspirin, its analogues and even unrelated chemical moieties could not be used in allergic disorders because of the precipitation of a pseudoallergic reaction in aspirin intolerant patients. Despite their anti-inflammatory effects, almost all NSAIDS potentiate $I_gE$-mediated histamine release from mast cells and basophils resulting in vasomotor rhinitis, urticaria and bronchial asthma in these patients (Bianco, S, Robuschi, M, Petrigni, G et al., *Drugs,* 46, 1993, 115–120).

However, one unique NSAID stands out from the rest. Nimesulide, a sulfonanilide NSAID, is well tolerated by patients with all allergic disorders and aspirin idiosyncrasy (Casolaro, V, Meliota, S, Marino, O et al., *J. Pharmacol. Exp. Ther.,* 267, 1993, 1375–1385). It has a profound antihistaminic, antianaphylactic activity (Berti, F, Rossoni, G, Buschi, A et al., *Arznemittel Forschung,* 40, 1990, 1011–1016). in addition to its potent anti inflammatory action (Serafin, W E, 1996; Bellusi, L, Passali, D, *Drugs* (46) *Suppl.* 1, 1993, 107–110). Nimesulide inhibits the allergen induced immunologic release of histamine and also improves bronchial responsiveness in asthmatic patients exposed to bronchoconstrictors (Casolaro, V, et al. 1993; Berti, F, et al. 1990).

All above studies only indicated the possible extension of antiinflammatory action of Nimesulide for control of inflammation of upper respiratory tract. However, the use of Nimesulide as an antiasthmatic due to antiallergic and leukotriene inhibiting activities of Nimesulide has not been reported so far, and by careful experimentation and application of scientific logic the inventors combined Nimesulide with Cetirizine in different proportions and carried out several experiments to see the utility of such a combination for use as an antiasthmatic agent. It has been surprisingly observed by the inventors and described in the present invention that a combination of Nimesulide with Cetirizine is a synergistic composition and of immense utility in asthma.

Other anti-inflammatory drugs used in chronic rhinitis, chronic bronchitis and bronchial asthma are cromolyn sodium, nedocromil and glucocorticoids. The glucocorticoid therapy is not without an accompanied risk of myriad side effects (Serafin, W E, 1996). Cromolyn sodium and nedocromil can only be given by inhalation, only about 1% of an oral dose of cromolyn is absorbed. Even when inhaled, cromolyn sodium has to be taken 4 times daily due to its short half-life of 45–100 minutes. Nedocromil is reported to leave a bad taste in mouth. Several other anti-inflammatory agents have been assessed, mainly as steroid-sparing agents. These include methotrexate, gold, troleandomycin, hydroxychloroquine, dapsone and cyclosporin. But their efficacy has not been firmly established (Szefler, S., Antiinflammatory drugs in the treatment of allergic diseases., Medical Clinics of North America, 76, 1992, 953–975).

U.S. Pat. No. 5,658,948 granted to ALLERGAN INC., discloses a formulation and method including an acceptable drug, such as Prostaglandins, Flurbiprofen, Keterolac Tromethamine, Cetirizine HCl, Indomethacin and Bufrolin, which are interactive with benzalkonium chloride to form a precipitate along with benzalkonium chloride acting as a preservative and an amino acid having enough positive charge at the pH of the formulation and/or Tromethamine present in an amount sufficient to interface with the interaction between the drug and benzalkonium chloride in order to maintain the preservative activity of the benzalkonium chloride. Further, the use of Lysine, L-arginine, or Histidine is also useful in reducing the cytotoxicity of the formulation.

U.S. Pat. No. 5,627,183 granted to SEPRACOR INC., discloses methods for utilizing optically pure (+) Cetirizine for the treatment of urticaria in humans while avoiding the concomitant liability of adverse effects associated with the racemic mixture of Cetirizine.

U.S. Pat. No. 5,419,898 granted to SENJU PHARMACEUTICAL Co., LTD., discloses an anti-allergic composition for opthalmic or nasal use, comprising cetirizine or a salt thereof as an active ingredient. The antiallergic composition may further contain a cyclodextrin compound, as well as surfactant and/or a water soluble polymer.

WO 9406429 granted to SEPRACOR INC., discloses methods and compositions utilizing optically pure (−) cetirizine for the treatment of seasonal and perennial allergic rhinitis in humans while avoiding the concomitant liability of adverse effects associated with the racemic mixture of cetirizine. The optically pure (−) isomer is also useful for the treatment of allergic asthma and chronic and physical urticaria. (−) Cetirizine is an inhibitor of eosinophil chemotaxis and is therefore useful in the treatment of other conditions related to eosinophilia such as allergic asthma, seasonal allergic rhinitis, atopic dermatitis, some parasitic diseases, some chronic obstructive lung diseases and certain gastrointestinal and genitourinary disorders.

No pharmacological composition has been reported in literature as well as no product is available where Nimesulide and salts thereof is employed in combination with second generation antihistamine. Fixed dose drug combinations are rapidly being re-introduced in clinical practice after several years of ostracism as these have the potential of acting synergistically and predictably.

It is the objective of the present invention to provide a novel antileukotriene, antihistaminic, anti-allergic and anti-inflammatory composition containing Nimesulide and salts thereof and Cetirizine.

It is the further objective of the present invention to provide a novel process for the manufacture of an antileukotriene, antihistaminic, anti-allergic and antiinflammatory composition containing Nimesulide and salts thereof and Cetirizine.

It is a further objective of the invention to provide a novel metered dose inhaler nasal delivery system for the above composition.

It is a further objective of the invention to provide a novel injectable delivery system of the above composition.

It is a further objective of the invention to provide a novel topical delivery system for the above composition.

It is a further objective of the invention to provide the above composition to be taken orally by way of a pedriatic suspension/capsule/tablet.

SUMMARY OF THE INVENTION

The present invention relates to a novel composition of Nimesulide and salts thereof and Cetrizine possessing antileukotriene, antihistaminic, antiallergic and antiinflammatory action.

The composition is useful in the cure of allergic disorders such as rhinitis, bronchitis, asthama, urticaria and the like.

DETAILED DESCRIPTION OF THE INVENTION

The following unique features of Nimesulide may prove to be quite beneficial in all allergic disorders.

1) Nimesulide is a potent stabilizer of mast cells and basophils. Thus, it prevents the release of histamine, proteases, TNF-a, Prostaglandins, leukotrienes, PAF and other cytokines from activated mast cells.

2) Nimesulide indirectly blunts the eosinophil deluge in asthmatic attacks because of its mast cell and basophil stabilizing property. Mast cells and basophils release an eosinophil chemotactic factor that causes eosinophils to migrate towards inflamed allergic tissue. Nimesulide is also reported to inhibit chemotaxis and synthesis of platelet activating factor and leukotrienes by human eosinophils.

3) Nimesulide potently inhibits the phosphodiesterase type IV in human polymorphonuclear leukocytes. The resultant increase in cAMP accounts for a marked decrease in chemotaxis, degranulation and free radical generation. PDE-IV inhibitors are finding a place as anti-asthmatic drugs.

4) Nimesulide inhibits the neutrophil respiratory burst and hence the release of free radicals, cytokines, eicosanoids, prostaglandins etc.

5) Nimesulide is a potent anti-oxidant. Hence it prevents tissue injury at sites of inflammation by maintaining natural host protective systems.

Second generation Histamine (H,receptor) antagonist (e.g. cetirizine, fexofenadine, acrivastine, astemizole, loratidine etc.) are the drugs of choice in the treatment of allergic rhinitis as they are long acting and are free from sedative and anticholinergic effects. In addition, second generation antihistamines have the following unusual and potentially beneficial properties.

1) These non-sedative anti-histamines have demonstrated dose-related protection against histamine induced bronchoconstriction.

2) These have been shown to protect against exercise, ultrasonic nebulized distilled water and cold air induced bronchoconstriction.

3) These produce modest but statistically significant acute bronchodilation in mild to moderate asthma.

4) Cetirizine is reported to have an anti inflammatory property in addition to its $H_1$-antagonizing action. Cetirizine inhibits inflammatory cell migration by potently inhibiting eosinophil influx and eosinophil degranulation.

5) ICAM-1 expression is a sensitive marker of mucosal allergic inflammation. ICAM-1 is also the receptor for most human rhinoviruses, which are the cause of more than 80% of asthmatic attacks in children. It has been reported that Cetirizine is able to modulate and down regulate ICAM −1 expression in epithelial cells.

6) Cetirizine is very effective in inhibiting the cutaneous early & late phase responses by inhibiting PAF and eosinophil recruitment in skin. In a recent report, almost 70% chronic hives patients reported excellent results on a daily regimen of 10 mg of cetirizine. Compared to other antihistamines cetirizine treatment produced faster, more potent and more long-lasting relief of wheals and flares.

7) Cetirizine does not cause cardiac arrythmias reported by some other antihistamines.

8) Continuous Cetirizine treatment is reported to be better than on-demand treatment in rhinitis sensitive to pollens.

Our findings as disclosed in this patent application indicate that sulfonanilide NSAIDs e.g. Nimesulide and thereof when combined with cetirizine forms an excellent synergistic antileukotriene, antihistaminic, anti-allergy and anti-inflammatory composition.

By careful experimentation the inventors have found that although Nimesulide does not block an exogenously administered histamine but very effectively blocks the release of histamine by stabilizing the mast cells and basophills as evident from egg albumin experiment as disclosed in the present invention.

The histamine released if any will be blocked by Cetirizine. Surprisingly, we also found out that Nimesulide as well as Cetirizine have a leukotriene action which is synergistic when the drugs are combined as evident from the Table. 3.

In accordance with the present invention there is disclosed a novel composition of Nimesulide and salts thereof and Cetirizine possessing antileukotriene, antihistaminic, anti-allergy and antiinflammatory action.

In accordance with a preferred embodiment of the invention the composition comprises Nimesulide from 1 to 53 parts, Cetirizine from 0.3 to 3.3 parts and pharmaceutical base and excipients from 44 to 98.5 parts.

The anti-inflammatory, antileukotriene, antihistaminic and antiallergic composition in accordance with the present invention can be in the form of a tablet, injection, once a day composition, metered dose inhaler, topical gel, capsules, sustained release tablets and the like.

The anti-inflammatory, antileukotriene, antihistaminic and antiallergic composition in accordance with the present invention is prepared by the process which comprises the following steps:

Nimesulide and Cetrizine are blended uniformly and passed through a fine sieve to reduce the particle size in the form of a fine powder and any of the following steps affected to obtain the product in the desired form;

1. the said uniform powder is blended with excipients at 25±2° C. temperature and 50%±5 Relative humidity and filled in empty gelatin capsules to yield capsule dosage form.
2. the uniform blend is granulated with granulating fluid at ambient conditions and dried at temperature not exceeding 60° C. for a period of time so as to yield moisture content around 1%. After reduction in size and lubrication, the granules are compressed into tablets at 25±2° C. temperature and 50%±5 Relative humidity.
3. the uniform blend is dissolved in suitable diluents and a gelling agent is added to form a topical gel or a transdermal gel.
4. the uniform blend is dissolved in a solvent suitable for parenteral administration. The solution is affected at temperature range of 25° C. to 35° C. under normal conditions of stirring. The solution is then filtered, sterilized and aseptically filled in ampoules. Alternatively, the ampoules are autoclaved at around 121° C. for a period of about 30 minutes.

Preferably the composition comprises Nimesulide and Cetrizine in the ratio of 1:5 to 1:40.

Preferably the granulating fluid for granulating the fine powdered blend of Nimesulide and Cetrizine is Maize starch and/or Polyvinylpyrrolidone.

Preferably the diluents and tgelling agent for dissolving the fine blend of Nimesulide and Cetrizine for topical and transdermal gel are Dimethylsulphoxide and/or dimethylacetamide and Carbopol and/or Hydroxypropyl cellulose.

Preferably the solvent for dissolving the uniform blend of Nimesulide and Cetrizine for parenteral administration is Water and/or dimethylacetamide.

Experiment to Study the Antiasthmatic Activity of Nimesulide and Cetirizine

Antiasthmatic activity of Nimesulide and Cetirizine was studied on histamine-induced, egg albumin-induced and leukotriene-$D_4$-induced brochospasm in guinea pig in vivo.

Materials & Method

Animals

Guinea pig 300–350 g either sex, housed in the Central Animal house of Panacea Biotec Ltd., Lalru and kept under standard laboratory conditions, were used.

Procedure

Urethane—anaesthetised, 18-h fasted guinea pigs 300–350 g were used. d-tubocurarine (3 mg/kg i.v) was administered to prevent spontaneous respiratory movements. Guinea pigs were artificially ventilated by a UGO Basile Rodent ventilator through a tracheal cannula at a rate of 60 strokes/min. and a stroke volume of 1 ml/100 g. Insufflation pressure was measured by attaching a pressure transducer (UGO Basile) to a Gemini two channel recorder (UGO Basile). A polyethylene catheter was inserted in the left jugular vein for iv administration of drugs. The animals were stabilized for 10 minutes.

% Insufflation pressure was calculated as the % increase in pressure due to constriction of the airways with respect to the basal pressure. Less % insufflation pressure denotes less bronchoconstriction caused due to the effect of test compounds with respect to the basal tone of the airways.

Drugs

Nimesulide and Cetirizine dihydrochloride (Panacea Biotec Ltd., India), Histamine, Leukotriene $D_4$ and Urethane (all from Sigma, USA), d-tubocurarine chloride (Diosynth, Netherlands), Egg albumin (Qualigens Fine Chemicals, Bombay). Cetirizine was dissolved in deionized water. Nimesulide was suspended in 0.25% Xanthum gum. Histamine and d-tubocurarine chloride were dissolved in saline and Leukotriene D4 was diluted with Methanol and Ammonium Acetate buffer in a ratio of 70:30 at a pH of 5.4.

Statistical Analysis

Unpaired students t-test was applied and p <0.05 and above were treated as significant.

Experimental Protocol

Group I Histamine Treated

Histamine challenge (5 □g/kg and 10 □g/kg iv) was given to the animal and increase in insufflation pressure was noted in the control group (Table. 1).

Test compounds (Nimesulide, Cetirizine, Nimesulide+ Cetirizine) were given 2 hours before histamine challenge in the test group. Any decrease in the insufflation pressure was noted (Table. 1).

Group II: Egg Albumin Treated

Guinea pigs were sensitized by injections of 100 mg of Egg albumin ip and 100 mg Egg albumin sc in saline. Guinea pigs were used after day 21st. Animals were challenged with 1 mg/kg and 2 mg/kg of Egg albumin and increase in insufflation pressure was noted (Table. 2).

Group III Leukotriene D4 Treated $LTD_4$ challenge (1 μg/kg and 2 μg/kg) was given to the animal and increase in insufflation pressure was noted in the control group (Table. 3).

Test compounds (Nimesulide, Cetirizine, Nimesulide+ Cetirizine) were given 2 hours before $LTD_4$ challenge in the test group. Any decrease in the insufflation pressure was noted (Table. 3) with respect to the control group.

Results

Cetirizine (1.66 mg/kg) significantly reduced the histamine (5 and 10 □g/kg) induced increase in insufflation pressure. Nimesulide (single dose, S, 11.66 mg/kg and double dose, D, 23.32 mg/kg) had no significant inhibitory effect on the insufflation pressure.

Combination of Nimesulide (single dose, S) and Cetirizine showed no significant effect whereas Nimesulide (double dose, D) and Cetirizine had potent antihistaminic effect.

Nimesulide (11.66 mg/kg) significantly reduced the egg albumin induced (1 mg/kg, 2 mg/kg) insufflation pressure, the effect of Nimesulide was 92.0 to 94.0%. Cetirizine (1.66 mg/kg) also reduced the insufflation pressure but it is slightly less than that of Nimesulide. In combination Nimesulide and Cetirizine also showed a highly significant effect as compared to the control (Table. 2).

Nimesulide (11.66 mg/kg) had no effect on the insufflation pressure whereas Cetirizine (1.16 mg/kg) significantly blocked $LTD_4$-induced contractions. Combination of Nimesulide (11.66 mg/kg) and Cetirizine (1.16 mg/kg) potently blocked the leukotriene induced contractions. Double dose Nimesulide (23.32 mg/kg) itself had a potent inhibitory effect on $LTD_4$-induced contractions. Combination of Nimesulide (23.32 mg/kg) and Cetirizine (1.16 mg/kg) had the maximum (□90%) inhibitory action on $LTD_4$-induced contractions (Table. 3).

Discussion

Cetirizine but not Nimesulide acts as a potent antihistaminic in guinea pig model of bronchoconstriction. Nimesulide double dose in combination with Cetirizine shows a potent antihistaminic effect which may be due to Cetirizine alone.

Hence Nimesulide itself has no antihistaminic action once histamine has been released to occupy the receptors. Nevertheless, Nimesulide can have an inhibitory effect on the pre-formed allergic mediators thus having an indirect antihistaminic action.

Preliminary study reports suggest that Nimesulide has a highly potent anti-allergic action in antigen (egg albumin) induced bronchospastic studies. Combination of Nimesulide and Cetirizine offer a dual protection in cases of allergic asthma, as Cetirizine is a potent antihistaminic. It is inferred that Nimesulide—Cetirizine combination can be used as a prophylactic for chronic allergic asthma.

Cetirizine and double-dose Nimesulide, both can block $LTD_4$-induced bronchoconstriction in guinea pigs. Combination of Cetirizine and Nimesulide is a very potent blocker of $LTD_4$-induced bronchoconstriction. This effect may be due to selective inhibition of phosphodiesterase (PDE) isozyme III and IV. Such inhibition has been shown substantially anti-inflammatory effects in vivo. PDE4 inhibitors act by inducing an increase in the intracellular levels of cAMP which in turn suppresses inflammatory cell activity and causes relaxation of airway smooth muscles. Nimesulide is reported to be a potent PDE IV inhibitor in vitro with an $IC_{50}$ □ 40 μM. That the combination is effectively blocking exogenously administered $LTD_4$ implies that either Nimesulide and Cetirizine have a combined PDE III and PDE IV isozyme inhibiting capacity or Nimesulide/ Cetirizine are working as $LTD_4$ receptor antagonists.

The inhibition, by this combination, of the antigen-induced (egg albumin) bronchoconstriction may also be through its capacity to act as a PDE III/IV inhibitor.

These preclinical results indicate the potential therapeutic efficacy of the combination of Nimesulide and Cetirizine in the treatment of allergic inflammatory airway disorders such as asthma.

Inference

As asthma is now viewed primarily as a chronic allergic disease with an underlying inflammatory activity the ideal antiasthmatic drug should possess the following three properties:

Antiallergic action

Anti Leukotriene action

Antihistaminic action

Nimesulide and Cetirizine when given together possess all the three properties as is evident from the following observations:

1. Cetirizine (1.16 mg/kg p.o) produces a decrease in % insufflation pressure by 42.86%, Nimesulide (23.32 mg/kg p.o) by 61.0% whereas Nimesulide+Cetirizine synergistically decrease the pressure by 80.21% in case of LTD4-induced bronchoconstriction in guinea pigs (Table. 3).

2. Cetirizine (1.16 mg/kg p.o) produces a decrease in % insufflation pressure by 70.52%, Nimesulide (11.66 mg/kg p.o) by 90.24% whereas Nimesulide+Cetirizine synergistically decrease the pressure by 96.57% in case of egg albumin induced bronchoconstriction in guinea pigs (Table. 2).

3. In case of histamine induced bronchoconstriction Cetirizine (1.16 mg/kg p.o) decreases the % insufflation pressure by 62.71% whereas Nimesulide shows no antihistaminic effect.

Hence a combination of these two is required to produce a synergistic action in case of 1 and 2 as stated above. In case of 3 any histamine which escapes the mast cell stabilizing action of Nimesulide and gets released would be blocked by Cetirizine to reach the receptor sites and bronchoconstriction would be prevented.

These preclinical results indicate a three pronged antiasthmatic action provided by the combination of Nimesulide and Cetirizine.

The inflammation associated with asthmatic decrease will be reduced by Nimesulide by selective COX-2 inhibition activity.

Therefore of this invention teaches an art of treating asthma by a combination of NSAID Nimesulide alongwith an antihistaminic drug Cetirizine and this combination due to a synergistically pharmacological action will have usefulness to elevate symptoms of asthmatic and related disorders in a much better fashion then the known agents for the drugs alone.

The invention will now be described with reference to the accompanying examples which are illustrative and by means should be construed to limit the scope of the invention.

| Example I: Tablets | | |
| --- | --- | --- |
| 1. | Nimesulide | 200 mg |
| 2. | Cetirizine dihydrochloride | 10 mg |
| 3. | Microcrystalline Cellulose | 100 mg |
| 4. | Maize Starch | 40 mg |
| 5. | PVP K-30 | 4 mg |
| 6. | Sodium Lauryl Sulphate | 1 mg |
| 7. | Magnesium Stearate | 4 mg |
| 8. | Colloidal Silicon Dioxide | 6 mg |
| 9. | Sodium Starch Glycollate | 10 mg |
| 10. | Purified Water | — |

Mix 1, 2, 3 & 4. Dissolve 5 & 6 in 10 and granulate the above and mix. Dry, soft and blend with 7, 8 & 9. Compress the tablets.

| Example II: Tablets | | |
| --- | --- | --- |
| 1. | Nimesulide | 200 mg |
| 2. | Cetirizine dihydrochloride | 5 mg |
| 3. | Microcrystalline Cellulose | 81 mg |
| 4. | Maize Starch | 30 mg |
| 5. | Polyoxyl 40 Hydrogenated Castor Oil | 1 mg |
| 6. | PVP K-30 | 2 mg |
| 7. | Magnesium Stearate | 2 mg |
| 8. | Colloidal Silicon Dioxide | 4 mg |
| 9. | Sodium Starch Glycollate | 5 mg |
| 10. | Purified Water | — |

Mix 1, 2, 3 & 4. Dissolve 5 & 6 in 10 and granulate the above and mix. Dry, soft and blend with 7, 8 & 9. Compress the tablets.

| Example III: Topical Gel | | |
| --- | --- | --- |
| 1. | Nimesulide | 1% |
| 2. | Cetirizine (Suitable Pharmaceutical form) | 0.5% |
| 3. | Carbopol | 1% |
| 4. | Hydroxypropyl Cellulose | 1.5% |
| 5. | PEG 400 | .25% |
| 6. | Dimethyl Sulphoxide | 15% |
| 7. | Isopropyl Alcohol | 40% |
| 8. | Hydrochloric Acid | q.s. to adjust pH |
| 9. | Propylene Glycol | 5% |
| 10. | Purified water | 10% |

Disperse 1 in 5, 6 and 9 separately. Dissolve 2 in 80% of 10. Disperse 3 & 4 in 7 with vigorous stirring. Add the two solutions to the dispersion. Allow to smell. Dilute 8 in remainder of 10 and adjust pH in the range of 2 to 6.

| Example IV: Capsules | | |
| --- | --- | --- |
| 1. | Nimesulide | 200 mg |
| 2. | Cetirizine dihydrochloride | 10 mg |
| 3. | Maize Starch | 80 mg |
| 4. | Sodium Lauryl Sulphate | 1.5 mg |
| 5. | Colloidal Silicon Dioxide | 3.5 mg |

Empty hard gelatin capsules. Sift 1, 3 & 5 through 30 mesh and 2 & 4 through 60 mesh. Mix uniformily and fill empty hard gelatin capsules at 295 mg.

| Example V: Sustained Release Bilayered Tablets | | |
| --- | --- | --- |
| A. | | |
| 1. | Nimesulide | 200 mg |
| 2. | Lactose | 100 mg |
| 3. | Hydroxypropylmethyl Cellulose | 35 mg |
| 4. | Polyoxyl 40 Hydrogenated Castor Oil | 2 mg / 2 mg |
| 5. | PVP K-30 | 4 mg |
| 6. | Magnesium Stearate | 2 mg |
| 7. | Colloidal Silicon Dioxide | 2 mg |
| 8. | Isopropyl Alcohol | 2 mg |

Mix 1, 2 & 3. Dissolve 4 & 5 in 8 and granulate the above and mix. Dry, soft and blend with 6 & 7.

| B. | | |
| --- | --- | --- |
| 1. | Cetirizine dihydrochloride | 10 mg |
| 2. | Lactose | 225 mg |
| 3. | Maize Starch | 55 mg |
| 4. | PVP K-30 | 3 mg |
| 5. | Magnesium Stearate | 3 mg |
| 6 | Sodium Starch Glycollate | 4 mg |
| 10. | Purified Water | — |

Mix 1, 2 & 3. Dissolve 4 in 10 and granulate the above and mix. Dry, soft and blend with 5 & 6. Compress the granules of A and B into bilayer tablets.

| Example VI : Nimesulide (in osmotic pump) + Cetirizine Tablets |
| --- |
| I Drug layer |

| | |
| --- | --- |
| Nimesulide | 200 mg |
| Sodium Chloride | 15 mg |
| Carbopol 934 P | 100 mg |
| Magnesium Stearate | 1 mg |
| Osmotic Layer | |
| Polyethylene Oil | 100 mg |
| Carboppl 974 P | 150 mg |
| Sodium Chloride | 10 mg |
| Magnesium Stearate | 1 mg |
| Iron Oxide Red | 0.5 mg |

The two layers are mixed separately and compressed into a bilayer tablet.

| II Casing Layer | |
| --- | --- |
| Cellulose Acetate | 4% |
| PEG 600 | 4% |
| Purified Water | 10% |
| Acetone | 82% |

Dissolved Cellulose acetate in the solvents. Added the plasticizer to the solution. Coated the bilayer tablet with casing layer of suitable thickness. An orifice was drilled into the drug layer.

| III Cetirizine Coating | |
|---|---|
| Cetirizine hydrochloride | 10 mg |
| Hydroxypropylmethyl Cellulose | 7 mg |
| PEG 400 | 0.5 mg |
| Isopropyl Alcohol | |
| Purified Water | |
| Iron oxide red | 0.05 mg |

Prepared a coating solution and coated the tablets of step II for 10 mg/ tablet Cetirizine dihydrochloride.

| Example VII: Metered dose inhaler | | |
|---|---|---|
| 1. | Nimesulide (within 1 to 5 microns) | 33% |
| 2. | Cetirizine dihydrochloride 3.3% (within 1 to 5 microns) | 3.3% |
| 3. | Lactose | 2% |
| 4. | Sorbitan Trioleate | 0.5% |

-continued

| Example VII: Metered dose inhaler | | |
|---|---|---|
| 5. | Propellant 114 | 30.60% |
| 6. | Propellant 12 | 30.60% |

Suspended 1, 2 & 3 in a mixture of 4, 5 % 6 and filled into metered dose inhalation assembling using cold filling apparatus as well known to people skilled in the art.

| Example VII: Injection | | |
|---|---|---|
| 1. | Nimesulide Potassium Salt | 2% |
| 2. | Cetirizine dihydrochloride | 0.33% |
| 3. | Benzyl Alcohol | 2% |
| 4. | Ethylene diamine tetracetate disodium salt | 0.002% |
| 5. | Water for injection | q.s. to 100% |

Dissolve 4 in 90% of 5 by heating up to 80° C. Add 3 and mix. Then add 1 and 2 and stir till a clear solution is formed. Make up the volume to 100% with 5. Filter through 0.22 $\mu$ nylon membrane filter and fill aseptically into vials/ampoules.

TABLE 1

Effect of Nimesulide, Cetirizine and combination on Histamine induced bronchoconstrictor in guinea pigs.

| | | | Histamine Challenge (% insufflation pressure) | |
|---|---|---|---|---|
| S.No. | Treatment (mg/kg p.o) | n | 5 $\mu$g/kg | 10 $\mu$g/kg |
| 1 | Control | 4 | 187.42 ± 22.49 | 239.07 ± 43.64 |
| 2 | Nimesulide 11.66 mg/kg p.o | 4 | 171.07 ± 23.76 | 236.47 ± 40.40 |
| 3 | Cetrizine 1.16 mg/kg p.o | 5 | 37.29 ± 6.76*** | 68.35 ± 18.20*** |
| 4 | Nimesulide 11.66 mg/kg p.o + Cetrizine 1.16 mg/kg p.o | 5 | 109.02 ± 32.03* | 165.86 ± 31.24 |
| 5 | Nimesulide 23.32 mg/kg p.o | 4 | 163.15 ± 43.27 | 205.10 ± 31.33 |
| 6 | Nimesulide 23.32 mg/kg p.o + Cetrizine 1.16 mg/kg p.o | 6 | 44.28 ± 10.54*** | 75.93 ± 15.74*** |

TABLE 2

Effect of Nimesulide, Cetirizine and combination on Antigen (egg albumin) induiced bronchoconstrictor in guinea pigs

| | | | % Insufflation pressure after egg albumin challange | |
|---|---|---|---|---|
| S.No. | Treatment (mg/kg p.o) | n | 1 mg/kg | 2 mg/kg |
| 1 | Control | 7 | 111.88 ± 110.53 | 196.90 ± 32.98 |
| 2 | Nimesulide 11.66 mg/kg p.o | 7 | 9.76 ± 4.17*** | 19.39 ± 4.32*** |
| 3 | Cetrizine 1.16 mg/kg p.o | 6 | 29.48 ± 10.85*** | 61.88 ± 20.97*** |
| 4 | Nimesulide 11.66 mg/kg p.o + Cetrizine 1.16 mg/kg p.o | 6 | 3.43 ± 1.17*** | 17.38 ± 9.41*** |

TABLE 3

6/37 Effect of Nimesulide, Cetirizine and combination on Leukotriene $D_4$ ($LTD_4$) induced bronchoconstrictor in guinea pigs.

| S. No. | Treatment (mg/kg p.o) | n | % Insufflation pressure after $LTD_4$ | |
|---|---|---|---|---|
| | | | 1 µg/kg $LTD_4$ | 2 µg/kg $LTD_4$ |
| 1 | Control | 3 | 186.02 ± 52.58 | 246.56 ± 14.33 |
| 2 | Nimesulide 11.66 mg/kg p.o | 3 | 192.45 ± 45.53 | 197.02 ± 37.76 |
| 3 | Cetrizine 1.16 mg/kg p.o | 1 | 57.14 | 92.85 |
| 4 | Nimesulide 11.66 mg/ko p.o + Cetrizine 1.16 mg/kg p.o | 4 | 60.00 ± 17.02*** | 96.07 ± 25.00*** |
| 5 | Nimesulide 23.32 mg/kg p.o | 3 | 38.99 ± 19.79*** | 140.07 ± 61.15* |
| 6 | Nimesuiide 23.32 mg/kg p.o + Cetrizine 1.16 mg/kg p.o | 4 | 19.79 ± 6.91 | 102.86 ± 31.33*** |

We claim:

1. A novel antileukotriene, antihistaminic, anti-allergy, antiinflammatory, and anti-allergic asthma composition comprising Nimesulide or salts thereof and Cetirizine or suitable pharmaceutical form thereof, in synergistic antileukotriene or anti-allergic asthma amounts.

2. The composition as claimed in claim 1 wherein Nimesulide is present in the composition from 1–53 parts, and Cetirizine is from 0.3–3.3 parts and wherein the composition additionally contains a pharmaceutical base and excipients of from 44–98.5 parts.

3. The composition as claimed in claim 1 wherein it is in the form selected from the group consisting of an injection, a topical delivery system, a pediatric suspension, capsules or tablet, bilayered tablets, sustained release tablets, topical gel, once a day composition, and metered dose inhaler.

4. The composition as claimed in claim 1 wherein it is in the form of a sustained release composition.

5. The composition as claimed in claim 4 wherein the sustained release composition is in the form of a bilayer tablet, and wherein the Nimesulide is in one layer of the bilayer and the Cetirizine is in the other layer of the bilayer.

6. The composition as claimed in claim 4 wherein the sustained release composition is in the form of a bilayer tablet formed by compressing a mixture of a layer containing the Nimesulide and an osmotic layer, wherein an orifice is drilled into the layer containing the Nimesulide, and wherein said bilayer tablet is coated with a casing layer, which casing layer is coated with a layer containing the Cetirizine.

7. The process for making a anti-inflammatory, antileukotriene, antihistaminic, antiallergic, and anti-allergic asthma composition comprising Nimesulide or salts thereof and Cetirizine or suitable pharmaceutical form thereof, which comprises blending Nimesulide and Cetirizine in synergistic antileukotriene or anti-allergic asthma amounts uniformly to form a mixture, and passing the mixture through a fine sieve to reduce the particle size to a fine powder, subjecting the said powder to any one or all the following steps to produce the desired product:

(a) blending the said uniform powder with excipients at 25±2° C. temperature and 50%±5 Relative humidity and filled in empty gelatin capsules to yield capsule dosage form;

(b) granulating the uniform blend at ambient conditions and drying at temperature not exceeding 60° C. for a period of time so as to yield moisture content around 1%, subjecting the resultant blend to reduction in size and lubrication, compressing into tablets at 25±2° C. temperature and 50%±5 Relative humidity;

(c) dissolving the uniform blend in suitable diluents and a gelling agent to form a topical gel or a transdermal gel;

(d) Dissolving the uniform blend in solvent suitable for parenteral administration at a temperature range of 25° C. to 35° C. under normal conditions of stirring, filtering and sterilizing the resultant solution.

8. The process as claimed in claim 7 wherein the composition comprises Nimesulide and Cetrizine in the ratio of 1:5 to 1:40.

9. The process as claimed in claim 7 wherein the granulating fluid for granulating the fine powdered blend of Nimesulide and Cetrizine is Maize starch and/or Polyvinylpyrrolidone.

10. The process as claimed in claim 7 wherein the diluents and gelling agent for dissolving the fine blend of Nimesulide and Cetrizine for topical and transdermal gel are (1) Dimethylsulphoxide and/or dimethylacetamide and (2) Carbopol and/or Hydroxypropyl cellulose.

11. The process as claimed in claim 7 wherein the solvent for dissolving the uniform blend of Nimesulide and Cetrizine for parenteral administration is Water and/or dimethylacetamide.

* * * * *

UNITED STATES PATENT AND TRADEMARK OFFICE
CERTIFICATE OF CORRECTION

PATENT NO. : 6,258,816 B1
DATED : July 10, 2001
INVENTOR(S) : Amarjit Singh et al.

Page 1 of 1

It is certified that error appears in the above-identified patent and that said Letters Patent is hereby corrected as shown below:

Title page,
Item [57], ABSTRACT, "Cetrizine" should read -- Cetirizine --.

Column 4,
Line 7, "Cetrizine" should read -- Cetirizine --.

Column 5,
Line 48, "Cetrizine" should read -- Cetirizine --.

Column 6,
Lines 7, 9, 12 & 16, "Cetrizine" should read -- Cetirizine --.

Column 12,
Line 15, "Example VII: Injection" should read -- Example VIII: Injection --;
Table 1, Column Treatment, S.No. 3, 4, 6, "Cetrizine" should read -- Cetirizine -;
Table 2, Title, "induiced" should read -- induced --;
Table 2, Column 1 mg/kg, "111.88 ± 110.53" should read -- 111.88 ± 10.53 --;
Table 2, Column Treatment, S. No. 3, 4, "Cetrizine" should read -- Cetirizine --.

Column 13,
Table 3, Column Treatment, S. No. 3, 4, 6, "Cetrizine" should read -- Cetirizine --.

Column 14,
Lines 38, 42, 47, 50 & 51, "Cetrizine" should read -- Cetirizine --.

Signed and Sealed this

Second Day of April, 2002

*Attest:*

*Attesting Officer*

JAMES E. ROGAN
*Director of the United States Patent and Trademark Office*